US008318651B2

(12) United States Patent
Hätzelt et al.

(10) Patent No.: US 8,318,651 B2
(45) Date of Patent: Nov. 27, 2012

(54) BIHETEROARYL METAL COMPLEXES AS BLEACH CATALYSTS

(75) Inventors: Andre Hätzelt, Düsseldorf (DE); Anette Nordskog, Sandefjord (NO); Stefan Leopold, Düsseldorf (DE); Peter Schmiedel, Düsseldorf (DE); Wolfgang von Rybinski, Düsseldorf (DE); Jörg Sundermeyer, Marburg (DE); Jan Döring, Marburg (DE)

(73) Assignee: Henkel AG & Co. KGaA (DE)

( * ) Notice: Subject to any disclaimer, the term of this patent is extended or adjusted under 35 U.S.C. 154(b) by 510 days.

(21) Appl. No.: 12/577,489

(22) Filed: Oct. 12, 2009

(65) Prior Publication Data

US 2010/0029540 A1   Feb. 4, 2010

Related U.S. Application Data

(63) Continuation of application No. PCT/EP2008/054350, filed on Apr. 10, 2008.

(30) Foreign Application Priority Data

Apr. 12, 2007 (DE) .......................... 10 2007 017 656

(51) Int. Cl.
C11D 1/00 (2006.01)
C11D 3/20 (2006.01)
C11D 3/28 (2006.01)

(52) U.S. Cl. ........ 510/311; 510/376; 510/492; 510/499; 510/500; 502/200; 502/324; 502/325; 252/186.33

(58) Field of Classification Search .................. 510/311, 510/376, 492, 499, 500; 502/200, 324, 325; 252/186.33
See application file for complete search history.

(56) References Cited

U.S. PATENT DOCUMENTS

| | | | |
|---|---|---|---|
| 5,614,161 A | 3/1997 | Wilkens et al. |
| 5,705,169 A | 1/1998 | Stein et al. |
| 5,730,960 A | 3/1998 | Stein et al. |
| 6,379,394 B1 | 4/2002 | Chilou et al. |
| 6,417,151 B1 | 7/2002 | Grothus et al. |
| 6,479,450 B1 | 11/2002 | Weiss et al. |
| 6,541,233 B1 | 4/2003 | Hillen et al. |
| 7,153,818 B2 | 12/2006 | Breves et al. |
| 7,262,042 B2 | 8/2007 | Weber et al. |
| 7,300,782 B2 | 11/2007 | Breves et al. |
| 7,303,905 B2 | 12/2007 | Breves et al. |
| 7,320,887 B2 | 1/2008 | Kottwitz et al. |
| 7,449,187 B2 | 11/2008 | Weber et al. |
| 7,510,859 B2 | 3/2009 | Wieland et al. |
| 7,569,226 B2 | 8/2009 | Weber et al. |
| 2003/0205707 A1 | 11/2003 | Chi-Ming |
| 2004/0235125 A1 | 11/2004 | Kottwitz et al. |
| 2004/0259222 A1 | 12/2004 | Breves et al. |
| 2005/0009167 A1 | 1/2005 | Weber et al. |
| 2005/0026269 A1 | 2/2005 | Kottwitz et al. |
| 2005/0049165 A1 | 3/2005 | Kottwitz et al. |
| 2005/0282261 A1 | 12/2005 | Sauter et al. |
| 2007/0128129 A1 | 6/2007 | Stehr et al. |
| 2009/0120555 A1 | 5/2009 | Breves et al. |
| 2009/0156454 A1 | 6/2009 | Schmiedel et al. |
| 2009/0170745 A1 | 7/2009 | Merkel et al. |

FOREIGN PATENT DOCUMENTS

| | | |
|---|---|---|
| CA | 2306376 A1 | 10/2000 |
| CA | 2326758 A1 | 10/2001 |
| DE | 2054019 A1 | 10/1971 |
| DE | 19601063 A1 | 9/1996 |
| DE | 19712033 A1 | 9/1998 |
| DE | 19721886 A1 | 12/1998 |
| DE | 19918267 A1 | 10/2000 |
| DE | 10138753 A1 | 3/2003 |
| DE | 102005053529 A1 | 6/2007 |
| DE | 102006018780 A1 | 10/2007 |
| DE | 102006022216 A1 | 11/2007 |
| DE | 102006022224 A1 | 11/2007 |
| EP | 0392592 B1 | 11/1994 |
| EP | 0357280 B1 | 2/1996 |
| EP | 0728749 A2 | 8/1996 |
| EP | 0693471 B1 | 1/1998 |
| EP | 0694521 B1 | 1/1998 |
| EP | 0818450 B1 | 1/1998 |
| WO | WO 91/02792 A1 | 3/1991 |
| WO | WO-92/21760 A1 | 12/1992 |
| WO | WO-95/23221 A1 | 8/1995 |
| WO | WO-95/32232 A1 | 11/1995 |
| WO | WO-96/04940 A1 | 2/1996 |
| WO | WO-96/29397 A1 | 9/1996 |
| WO | WO-96/34092 A2 | 10/1996 |
| WO | WO-97/14804 A1 | 4/1997 |
| WO | WO-97/24177 A1 | 7/1997 |
| WO | WO-97/31085 A1 | 8/1997 |

(Continued)

OTHER PUBLICATIONS

Orejon et al, "Oxidative carbonylation of aniline with new cobalt catalytic systems", Can. J. Chem., 83, p. 764-768, 2005.*
Pun et al, iron(I) complexes of 2,9-bis(2-hydroxyphenyl)-1,10-phenanthroline (H2dophen) as electrocatalysts for carbon dioxide reduction, The royal Society of Chemisty, p. 575-583, 2002.*
Routier S, et al., "Synthesis of metal complexes of 2,9-bis(2-hydroxyphenyl)-1,10-phenanthroline and their DNA binding and cleaving activities", J. Chem. Soc., Perkin Trans. 2, 1998, No. 2, pp. 863-868.
Giblin G. M. P., et al., "6,6'-Bis(2-hydroxyphenyl)-2,2'-bipyridine Manganese(III) Complexes: A Novel Series of Superoxide Dismutase and Catalase Mimetics". Bioorganic & Medicinal Chemistry Letters, 2001, vol. 11, pp. 1367-1370.
Lin, et al., "Structural, Photophysical, and Electrophosphorescent Properties of Platinum(II) Complexes Supported by Tetradentate N2O2 Chelates". Chem. Eur. J., 2003, vol. 9, No. 6, pp. 1263-1272.

(Continued)

Primary Examiner — Gregory Delcotto
(74) Attorney, Agent, or Firm — Connolly Bove Lodge & Hutz LLP

(57) ABSTRACT

Biheteroaryl metal complexes and the use thereof as bleach catalysts are described.

12 Claims, No Drawings

FOREIGN PATENT DOCUMENTS

| | | | |
|---|---|---|---|
| WO | WO-98/12307 | A1 | 3/1998 |
| WO | WO-98/45398 | A1 | 10/1998 |
| WO | WO-99/06573 | A1 | 2/1999 |
| WO | WO-99/64554 | A1 | 12/1999 |
| WO | WO-00/09512 | A2 | 2/2000 |
| WO | WO-01/38471 | A1 | 5/2001 |
| WO | WO-02/10356 | A2 | 2/2002 |
| WO | WO-02/44350 | A2 | 6/2002 |
| WO | WO-02/088340 | A2 | 11/2002 |
| WO | WO-03/002711 | A2 | 1/2003 |
| WO | WO-03/038082 | A2 | 5/2003 |
| WO | WO-03/054177 | A2 | 7/2003 |
| WO | WO-03/054184 | A1 | 7/2003 |
| WO | WO-03/054185 | A1 | 7/2003 |
| WO | WO-03/055974 | A2 | 7/2003 |
| WO | WO-03/056017 | A2 | 7/2003 |
| WO | WO-2004/058955 | A2 | 7/2004 |
| WO | WO-2004/058961 | A1 | 7/2004 |
| WO | WO-2005/056782 | A2 | 6/2005 |
| WO | WO-2005/124012 | A1 | 12/2005 |
| WO | WO-2008/125590 | A1 | 10/2008 |

OTHER PUBLICATIONS

Couchman et al., "Synthesis and coordination chemistry of the tetradentate ligands 6,6'-bis(3-pyrazolyl)-2,2'-bipyridine and 6,6'-bis(2-hydroxyphenyl)-2,2'-bipyridine: Intramolecular hydrogen-bonding in complexes of Cu(II), and a dinuclear double helicate with Ag(I)". Polyhedron, 1999, vol. 18, pp. 2633-2640.

Geissman et al., "The synthesis of some intermediates for use in the preparation of analogs of salicylaldehyde ethylenediimine cobalt ("salcomine")". J. Org. Chem. 1946, vol. 11, pp. 741-750.

Koning et al., "Synthesis and complexation characteristics of phenanthroline and bipyridine diols", ARKIVOC2004(II), pp. 189-205, (2004).

Lam et al., "Synthesis of Dinucleating Phenanthroline-Based Ligands". Tetrahedron, 1999, vol. 55, pp. 8377-8384.

Wallhauser in "Praxis der Sterilisation, Desinfektion—Konservierung: Keimidentifizierung—betriebshygiene". 1995, 5-th edition—Stuttgart; New York: Thieme.

Finkel P., "Formulierung kosmetischer Sonnenschutzmittel". SOFW-Journal, 1996, vol. 122, pp. 543-548.

* cited by examiner

BIHETEROARYL METAL COMPLEXES AS BLEACH CATALYSTS

CROSS-REFERENCE TO RELATED APPLICATIONS

This application is a continuation of and claims benefit of priority under 35 U.S.C. §120 of International Application No. PCT/EP2008/054350, filed on Apr. 10, 2008 (designating the U.S.), which in turn claims priority under 35 U.S.C. §119(a)-(d) of German Application No. DE 102007017656.4, filed on Apr. 12, 2007, the entire contents of each of which are incorporated herein by reference

BACKGROUND OF THE INVENTION

If bleaching with hydrogen peroxide is to be effective, it must be converted into a species with a greater bleaching action. One possibility for producing activated peroxy compounds involves using peracid precursors, or "bleaching activators" as they are known, such as for example TAED, which are converted into the active species by perhydrolysis.

A further possibility for producing activated species involves enzymatically catalyzed perhydrolysis of carboxylic acid esters or nitrile compounds using perhydrolases.

Finally, it is also known to use bleach catalysts for producing activated species, a bleach catalyst being taken to mean a substance which is capable of improving the bleaching performance of hydrogen peroxide on a bleachable substance without itself participating stoichiometrically in the reaction.

The use of bleach catalysts has the advantage over the other bleach activation methods that substoichiometric quantities of the compound are sufficient, whereby savings in volume and weight can be achieved in formulating the bleach-containing product. A reduction in weight, especially in washing and cleaning applications, is furthermore also associated with the advantage that inputs of substances into the environment are reduced, which is particularly advantageous on ecological grounds. In addition, savings in transport and packaging costs may also be made as a consequence.

It should furthermore be borne in mind that, when bleaching activators such as nitrites or TAED are used in the presence of water, premature hydrolysis may occur, whereas this problem may very largely be avoided when bleach catalysts are used. Furthermore, the occurrence of acids arising from the peracids in non-catalytic bleach activation results in a shift in the pH value, which may have an unfavorable impact on bleaching performance. Moreover, the bleaching performance of most bleaching activators is often inadequate at low temperatures.

For the above-stated reasons, the use of bleach catalysts is of particular interest in contrast with other bleach activation methods, such that there is, in principle, a need for new bleach catalysts.

Metal complexes of organic ligands such as salenes, saldimines, tris[salicylideneaminoethyl]amines, monocyclic polyazaalkanes, cross-bridged polycyclic polyazaalkanes, terpyridines and tetraamido ligands are in particular described as bleach catalysts. However, one disadvantage of the described metal complexes is that, in particular at low temperature, they either do not exhibit adequate bleaching performance or alternatively, in the case of adequate bleaching performance, unwanted damage to colors and possibly to textile fibers occurs.

Some biheteroaryl derivatives which are usable according to the invention have already been described in the prior art. WO 00/09512 and Giblin et al (Bioorganic & Medicinal Chemistry Letters 11 (2001) 1367-1370) accordingly describe 6,6'-bis-substituted 2,2'-bipyridines and also manganese complexes of these compounds. These manganese complexes are stated to exhibit superoxide dismutase and catalase activity, while possible applications are stated to be use as antioxidants in the medical field.

US 2003/0205707 and Lin et al. (Chem. Eur. J. 9 (2003) 1263-1272) describe platinum complexes, Couchma et al. (Polyhedron 18 (1999) 2633-2640) copper-complexes and Geissman et al. (J. Org. Chem. 11 (1946) 741-750) cobalt complexes of such ligands. One possible application for the platinum complexes is stated to be use as a dopant in a light-emitting device.

In particular, some phenanthroline derivatives usable according to the invention have also already been described by Koning et al. (ARKIVOC 2004(ii) 189-205, ISSN 1424-6376), Lam et al. (Tetrahedron 55 (1999) 8377-8384) and Routier et al. (J. Chem. Soc., Perkin Trans. 2 (1998) 863-868). Routier et al. describe copper, nickel, manganese and cobalt complexes of these ligands and the use thereof for cleaving nucleic acids. Lam et al. describe copper and nickel complexes and Koning et al. describe copper and zinc complexes of the ligands described in each case.

The stated documents do not describe the use of the ligands and metal-ligand complexes as bleach catalysts or as additives for washing or cleaning agents.

BRIEF SUMMARY OF THE INVENTION

The present invention relates to biheteroaryl metal complexes and to the use thereof as bleach catalysts.

It has surprisingly now been found that metal complexes of biheteroaryl derivatives are highly suitable as bleach catalysts and simultaneously have a more gentle action on laundry than do currently used bleach catalysts.

The present invention accordingly firstly provides washing or cleaning agents containing substituted biheteroaryl ligands and biheteroaryl-ligand complexes of biheteroaryl ligands of the general formula (I)

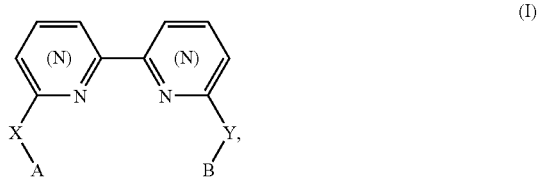

X and Y mutually independently denote ethyl, ethenyl, —CH=N—, —C($C_{1-18}$-alkyl)=N—, cycloalkyl, cycloheteroalkyl, $C_{6-10}$ aryl or heteroaryl, A and B mutually independently denote OH, SH, $NH_2$, NH($C_{1-18}$-alkyl) or N($C_{1-18}$-alkyl)$_2$, A is linked by X and B by Y to the biheteroaryl residue via 2 atoms, and in which the so formed skeleton can also be bridged as well as mono- or polysubstituted by further substituents, and (N) meaning that one or two CH groups of the corresponding aryl residue may optionally be replaced by N.

The substituted biheteroaryl ligand may in particular be a ligand selected from the following ligands:

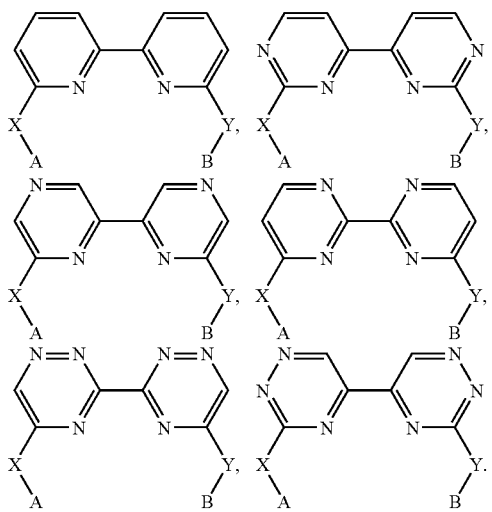

the ligand possibly being in each case correspondingly bridged and mono- or polysubstituted by further substituents.

Examples which may in particular be stated are the ligands baobipy and bfobipy:

baobipy bfobipy

The bridged biheteroaryl ligand preferably comprises a ligand of the general formula (II)

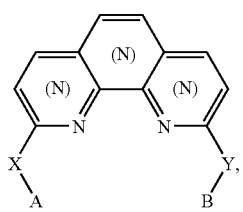

(II)

the skeleton formed in this manner also possibly being mono- or polysubstituted.

The bridged biheteroaryl ligand may in particular be selected from the following group:

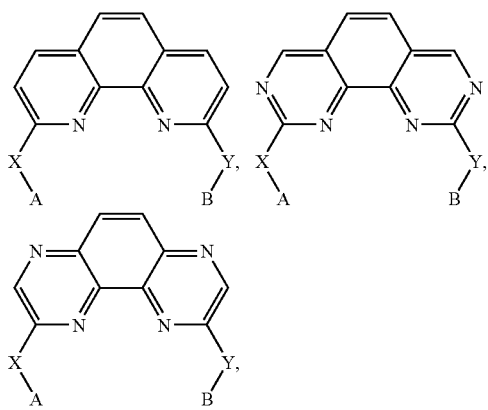

the skeleton formed in this manner also possibly being mono- or polysubstituted.

Examples which may in particular be mentioned are the ligands baophen and bfophen:

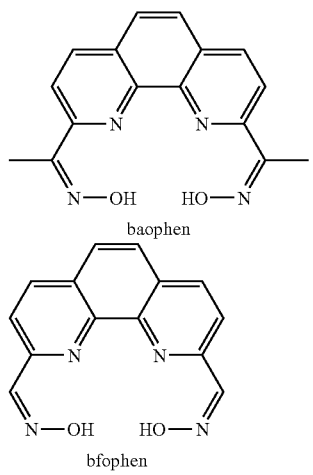

In a preferred embodiment, X and Y mutually independently denote $C_{6-10}$ aryl or heteroaryl and A and B denote OH or SH.

X and Y are preferably selected from optionally substituted benzene, naphthalene, pyrrole, furan, thiophene, pyridine, pyrimidine, pyrazine, pyrone, pyridone, purine, triazine, imidazole, thiazole, oxazole, indole, quinoline, isoquinoline, benzimidazole, benzothiazole and benzoxazole.

In a further preferred embodiment, the biheteroaryl ligand according to the invention is a ligand of the general formula (III)

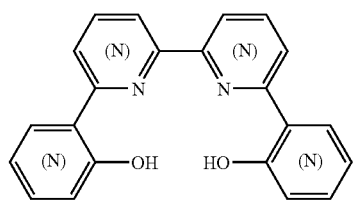

(III)

the skeleton formed in this manner also possibly being bridged and mono- or polysubstituted.

The bridged biheteroaryl ligand may in particular be a ligand of the general formula (IV)

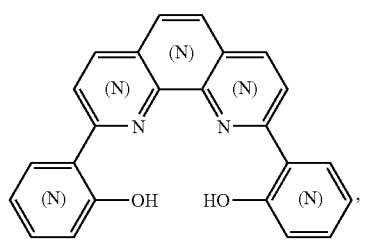

(IV)

the skeleton formed in this manner also possibly being mono- or polysubstituted.

In a particularly preferred embodiment, the substituted biheteroaryl ligand is a substituted phenanthroline ligand of the general formula (V)

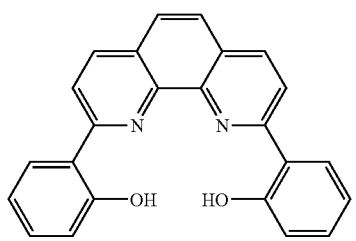

(V)

the skeleton formed in this manner also possibly being mono- or polysubstituted.

The substituents, which may be attached to the above-stated basic structures, may in particular be selected from alkyl, in particular $C_{1-22}$ alkyl, preferably $C_{1-18}$ alkyl, trifluoromethyl, cycloalkyl, in particular $C_{3-8}$ cycloalkyl, cycloalkylalkyl, in particular $C_{3-8}$-cycloalkyl-$C_{1-12}$-alkyl, alkenyl, in particular $C_{2-18}$ alkenyl, alkynyl, in particular $C_{2-18}$ alkynyl, heteroalkyl, heterocycloalkyl, alkoxy, in particular $C_{1-18}$ alkoxy, alkylsulfanyl, in particular $C_{1-18}$ alkylsulfanyl, alkylsulfinyl, in particular $C_{1-18}$ alkylsulfinyl, alkylsulfonyl, in particular $C_{1-18}$ alkylsulfonyl, alkanoyl, in particular $C_{1-18}$ alkanoyl, alkanoyloxy, in particular $C_{1-18}$ alkanoyloxy, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, hydroxy, amino, aryl, in particular $C_{6-10}$ aryl, arylalkyl, in particular $C_{6-10}$-aryl-$C_{1-12}$-alkyl, aryloxy, in particular $C_{6-10}$ aryloxy, arylsulfanyl, in particular $C_{6-10}$ arylsulfanyl, arylsulfinyl, in particular $C_{6-10}$ arylsulfinyl, arylsulfonyl, in particular $C_{6-10}$ arylsulfonyl, arylcarbonyl, in particular $C_{6-10}$ arylcarbonyl, arylcarbonyloxy, in particular $C_{6-10}$ arylcarbonyloxy, aryloxycarbonyl, in particular $C_{6-10}$ aryloxycarbonyl, arylaminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-$C_{1-12}$-alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl, heteroarylsulfanylcarbonyl, alkoxysulfonyl, in particular $C_{1-18}$ alkoxysulfonyl, alkoxycarbinol, in particular $C_{1-12}$ alkoxycarbinol, ammonium, hydroxycarbonyl, alkoxycarbonyl, in particular $C_{1-18}$ alkoxycarbonyl, aryloxycarbonyl, in particular $C_{6-10}$ aryloxycarbonyl, amidocarbonyl, halogen, in particular chlorine, bromine, iodine or fluorine, nitro, sulfato, sulfo, amidosulfo, phosphato, phosphono, amidophosphono, formyl, thioformyl, —(CH$_2$—CH$_2$—O—)$_n$H and —(CH$_2$—CH$_2$—CH$_2$—O)$_n$H with n=1 to 20, preferably 3 to 20, any of the residues of the resultant molecule, in particular the aliphatic and aromatic residues, also possibly being in each case mutually independently optionally mono- or polysubstituted, in particular mono-, di- or tri-substituted, preferably mono-substituted, in particular by substituents selected from the above-stated residues.

The substituents which may be attached to the parent structure are preferably selected from alkyl, in particular $C_{1-22}$ alkyl, preferably $C_{1-18}$ alkyl, cycloalkyl, in particular $C_{3-8}$ cycloalkyl, cycloalkylalkyl, in particular $C_{3-8}$-cycloalkyl-$C_{1-12}$-alkyl, alkenyl, in particular $C_{2-18}$ alkenyl, alkynyl, in particular $C_{2-18}$ alkynyl, heteroalkyl, heterocycloalkyl, alkoxy, in particular $C_{1-18}$ alkoxy, alkanoyl, in particular $C_{1-18}$ alkanoyl, alkoxycarbonyl, in particular $C_{1-18}$ alkoxycarbonyl, alkylaminocarbonyl, in particular $C_{1-18}$ alkylaminocarbonyl, alkylsulfanylcarbonyl, in particular $C_{1-18}$ alkylsulfanylcarbonyl, hydroxy, amino, alkylamino, in particular ($C_{1-18}$-alkyl)NH or di-($C_{1-18}$-alkyl)N, aryl, in particular $C_{6-10}$ aryl, arylalkyl, in particular $C_{6-10}$-aryl-$C_{1-12}$-alkyl, arylcarbonyl, in particular $C_{6-10}$ arylcarbonyl, aryloxycarbonyl, in particular $C_{6-10}$ aryloxycarbonyl, arylaminocarbonyl, in particular $C_{6-10}$ arylaminocarbonyl, arylsulfanylcarbonyl, in particular $C_{6-10}$ arylsulfanylcarbonyl, heteroaryl, heteroarylalkyl, in particular heteroaryl-$C_{1-12}$-alkyl, heteroarylcarbonyl, heteroaryloxycarbonyl, heteroarylaminocarbonyl, heteroarylsulfanylcarbonyl, trifluoromethyl, ammonium, hydroxycarbonyl, alkoxycarbonyl, in particular $C_{1-18}$ alkoxycarbonyl, aryloxycarbonyl, in particular $C_{6-10}$ aryloxycarbonyl, amidocarbonyl, halogen, in particular chlorine, bromine, iodine or fluorine, nitro, sulfato, sulfo, amidosulfo, phosphate, phosphono, amidophosphono, formyl, thioformyl, —(CH$_2$—CH$_2$—O—)$_n$H and —(CH$_2$—CH$_2$—CH$_2$—O)$_n$H with n=1 to 20, preferably 3 to 20, any of the residues of the resultant molecule, in particular the aliphatic and aromatic residues, also possibly being in each case mutually independently optionally mono- or polysubstituted, in particular mono-, di- or tri-substituted, preferably mono-substituted, in particular by substituents selected from the above-stated residues.

In a particularly preferred embodiment, the substituents which may be attached to the parent structure comprise substituents which increase the solubility of the ligand in an aqueous medium. In a particularly preferred embodiment, at least one substituent comprising an ammonium, hydroxycarbonyl, alkoxycarbonyl, aryloxycarbonyl, amidocarbonyl, halogen, nitro, sulfato, sulfo, amidosulfo, phosphato, phosphono, amidophosphono, hydroxy, alkoxy, amino or polyoxyethylene residue is accordingly attached to the ligands according to the invention. The substituent may in particular comprise the particular residue itself or an alkyl group, onto which the particular residue is attached, such that the substituent is particularly preferably selected from sulfo, sulfoalkyl, in particular sulfo-$C_{1-18}$-alkyl, hydroxycarbonyl, hydroxycarbonylalkyl, in particular hydroxycarbonyl-$C_{1-18}$-alkyl, phosphono, phosphonoalkyl, in particular phosphono-$C_{1-18}$-alkyl, hydroxy, hydroxyalkyl, in particular hydroxy-$C_{1-18}$-alkyl, amino, aminoalkyl, in particular amino-$C_{1-18}$-alkyl, halogen, haloalkyl, in particular halo-$C_{1-18}$-alkyl, —(CH$_2$—CH$_2$—O—)$_n$H and $C_{1-18}$-alkyl-(CH$_2$—CH$_2$—O—)$_n$H with n in each case being 1 to 20, preferably 3 to 20.

DETAILED DESCRIPTION OF THE INVENTION

According to the invention, $C_{1-18}$ alkyl in each case mutually independently denotes any saturated linear and branched alkyl residues with up to 18 C atoms, $C_{1-6}$ alkyl residues being preferred. According to the invention, $C_{1-6}$ alkyl denotes any saturated linear and branched alkyl residues with up to 6 C atoms, in particular methyl, ethyl, n-propyl, i-propyl, n-butyl, i-butyl, t-butyl and any isomers of pentyl and of hexyl.

According to the invention, $C_{3-8}$ cycloalkyl in each case mutually independently denotes any cyclic alkyl residues with 3 to 8 C atoms, preferably with 5 to 6 C atoms, the residues possibly being saturated or unsaturated, in particular denotes cyclopentyl, cyclohexyl or cyclopentadienyl.

According to the invention, $C_{2-18}$ alkenyl in each case mutually independently denotes any linear and branched alkyl residues with up to 18 C atoms which contain at least one double bond, $C_{2-6}$ alkenyl residues being preferred. According to the invention, $C_{2-6}$ alkenyl denotes any linear and branched alkyl residues with up to 6 C atoms which contain at least one double bond, in particular ethenyl, propenyl, i-propenyl and any isomers of butenyl, pentenyl and hexenyl.

According to the invention, $C_{2-18}$ alkynyl in each case mutually independently denotes any linear and unbranched alkyl residues with up to 18 C atoms which contain at least one triple bond, $C_{2-16}$ alkynyl residues being preferred. According to the invention, $C_{2-6}$ alkynyl denotes any linear and unbranched alkyl residues with up to 6 C atoms which contain at least one triple bond, in particular ethynyl, propynyl, i-propynyl and any isomers of butynyl, pentynyl and hexynyl.

According to the invention, heteroalkyl in each case mutually independently denotes any saturated and mono- or polyunsaturated, linear or branched alkyl residues which contain at least one, preferably exactly one heteroatom, in particular selected from O, S and N, the sum of C atoms and heteroatoms preferably amounting to up to 18, particularly preferably up to 6.

According to the invention, heterocycloalkyl in each case mutually independently denotes any cyclic alkyl residues which contain at least one, preferably exactly one, heteroatom, in particular selected from O, S or N, the ring preferably being three- to eight-membered, particularly preferably five- to six-membered. Examples of these are tetrahydrofuranyl, tetrahydrothiophenyl, pyrrolidinyl, 2-thiazolinyl, tetrahydrothiazolyl, tetrahydrooxazolyl, piperidinyl, piperazinyl, morpholinyl and thiomorpholinyl.

According to the invention, $C_{1-18}$ alkoxy in each case mutually independently denotes any saturated and unsaturated, linear and branched alkyl residues with up to 18 C atoms which are attached via an oxygen atom, $C_{1-6}$ alkoxy residues being preferred. According to the invention, $C_{1-6}$ alkoxy in each case mutually independently denotes any saturated and unsaturated, linear and branched alkyl residues with up to 6 C atoms which are attached via an oxygen atom, in particular methoxy and ethoxy.

According to the invention, $C_{1-18}$ alkylsulfanyl in each case mutually independently denotes any saturated and unsaturated, linear and branched alkyl residues with up to 18 C atoms which are attached via a sulfur atom, $C_{1-6}$ alkylsulfanyl residues being preferred. According to the invention, $C_{1-6}$ alkylsulfanyl denotes any saturated and unsaturated, linear and branched alkyl residues with up to 6 C atoms which are attached via a sulfur atom, in particular methylsulfanyl and ethylsulfanyl.

According to the invention, $C_{1-18}$ alkylsulfinyl in each case mutually independently denotes any saturated and unsaturated, linear and branched alkyl residues with up to 18 C atoms which are attached via an SO group, $C_{1-6}$ alkylsulfonyl residues being preferred. According to the invention, $C_{1-6}$ alkylsulfinyl denotes any saturated and unsaturated, linear and branched alkyl residues with up to 6 C atoms which are attached via an SO group, in particular methylsulfinyl and ethylsulfinyl.

According to the invention, $C_{1-18}$ alkylsulfonyl in each case mutually independently denotes any saturated and unsaturated, linear and branched alkyl residues with up to 18 C atoms which are attached via an $SO_2$ group, $C_{1-6}$ alkylsulfoxidyl residues being preferred. According to the invention, $C_{1-6}$ alkylsulfonyl denotes any saturated and unsaturated, linear and branched alkyl residues with up to 6 C atoms which are attached via an $SO_2$ group, in particular methylsulfonyl and ethylsulfonyl.

According to the invention, $C_{1-18}$ alkanoyl in each case mutually independently denotes any saturated and unsaturated, linear and branched alkyl residues with up to 18 C atoms which are attached via a carbonyl group, $C_{1-6}$ alkanoyl residues being preferred. According to the invention, $C_{1-6}$ alkanoyl denotes any saturated and unsaturated, linear and branched alkyl residues with up to 6 C atoms which are attached via a carbonyl group, in particular methylcarbonyl and ethylcarbonyl.

According to the invention, $C_{1-18}$ alkanoyloxy in each case mutually independently denotes any saturated and unsaturated, linear and branched alkyl residues with up to 18 C atoms which are attached via a carbonyloxy group, $C_{1-6}$ alkanoyloxy residues being preferred. According to the invention, $C_{1-6}$ alkanoyloxy denotes any saturated and unsaturated, linear and branched alkyl residues with up to 6 C atoms which are attached via a carbonyloxy group, in particular methanoyloxy, ethanoyloxy, n-propanoyloxy and i-propanoyloxy.

According to the invention, $C_{1-18}$ alkoxycarbonyl in each case mutually independently denotes any saturated and unsaturated, linear and branched alkyl residues with up to 18 C atoms which are attached via an oxycarbonyl group, $C_{1-6}$ alkoxycarbonyl residues being preferred. According to the invention, $C_{1-6}$ alkoxycarbonyl denotes any saturated and unsaturated, linear and branched alkyl residues with up to 6 C atoms which are attached via an oxycarbonyl group, in particular methoxycarbonyl and ethoxycarbonyl.

According to the invention, $C_{1-18}$ alkylaminocarbonyl in each case mutually independently denotes an aminocarbonyl group, which is mono- or disubstituted by a saturated or unsaturated, linear or branched alkyl residue with up to 18 C atoms, with aminocarbonyl residues mono- or disubstituted by $C_{1-6}$ alkyl groups, in particular monomethylaminocarbonyl, dimethylaminocarbonyl, monoethylaminocarbonyl and diethylaminocarbonyl, being preferred.

According to the invention, $C_{1-18}$ alkylsulfanylcarbonyl in each case mutually independently denotes any saturated and unsaturated, linear and branched alkyl residues with up to 18 C atoms which are attached via a thiocarbonyl group, $C_{1-6}$ alkylsulfanylcarbonyl residues being preferred. According to the invention, $C_{1-6}$ alkylsulfanylcarbonyl denotes any saturated and unsaturated, linear and branched alkyl residues with up to 6 C atoms which are attached via a thiocarbonyl group, in particular methylthiocarbonyl and ethylthiocarbonyl.

According to the invention, ($C_{1-18}$-alkyl)NH in each case mutually independently denotes any saturated and unsaturated, linear and branched alkyl residues with up to 18 C atoms which are attached via a hydrogenamino group, ($C_{1-6}$-alkyl)NH being preferred. According to the invention, ($C_{1-6}$-alkyl)NH denotes any saturated and unsaturated, linear and branched alkyl residues with up to 6 C atoms which are attached via a hydrogenamino group, in particular $CH_3NH$ and $C_2H_5NH$.

According to the invention, di-($C_{1-18}$-alkyl)N in each case mutually independently denotes any saturated and unsaturated, linear and branched alkyl residues with up to 18 C atoms which are attached via a ($C_{1-18}$-alkyl)amino group, di-($C_{1-6}$-alkyl)N being preferred. The two alkyl residues may here be identical to or different from one another. According to the invention, di-($C_{1-6}$-alkyl)N denotes any saturated and unsaturated, linear and branched alkyl residues with up to 6 C atoms which are attached via a ($C_{1-6}$-alkyl)amino group, in particular $(CH_3)_2N$ and $(C_2H_5)_2N$.

According to the invention, $C_{6-10}$ aryl, in particular also in $C_{6-10}$-aryl-$C_{1-12}$-alkyl, $C_{6-10}$ aryloxy, $C_{6-10}$ arylamino, $C_{6-10}$ arylsulfanyl, $C_{6-10}$ arylsulfonyl, $C_{6-10}$ arylsulfoxidyl, $C_{6-10}$ arylcarbonyl, $C_{6-10}$ arylcarbonyloxy, $CO_{6-10}$ aryloxycarbonyl, $C_{6-10}$ arylaminocarbonyl and $C_{6-10}$ arylsulfanylcarbonyl, preferably denotes phenyl or naphthyl, particularly preferably phenyl.

According to the invention, heteroaryl, in particular also in heteroaryl-$C_{1-12}$-alkyl, heteroaryloxy, heteroarylamino, heteroarylsulfanyl, heteroarylsulfonyl, heteroarylsulfoxidyl, heteroarylcarbonyl, heteroarylcarbonyloxy, heteroaryloxycarbonyl, heteroarylaminocarbonyl and heteroarylsulfanylcarbonyl, unless otherwise stated, denotes an aromatic residue with 5 to 10, preferably 5 or 6, ring members and containing at least one heteroatom selected from O, S and N, preferably selected from furanyl, thienyl, thiophenyl, pyrrolyl, isopyrrolyl, pyrazolyl, imidazolyl, oxazolyl, thiazolyl, isothiazolyl, pyridinyl, pyridazinyl, pyrimidinyl, pyrazinyl, triazinyl, benzofuranyl, benzothiophenyl, indolyl, quinolinyl, isoquinolinyl, benzimidazolyl, indazolyl, pyridofuranyl and pyridothienyl.

The alkyl residue in $C_{6-10}$-aryl-$C_{1-12}$-alkyl and heteroarylalkyl may be saturated or unsaturated, branched or unbranched. Preferred residues are benzyl, phenylethyl, naphthylmethyl and naphthylethyl.

According to the invention, "amino" denotes any desired substituted or unsubstituted amino group, in particular —$NH_2$, —$NH(C_{1-18}$-alkyl), —$N(C_{1-18}$-alkyl$)_2$, —$NH(C_{6-10}$-aryl) or —$N(C_{6-10}$-aryl$)_2$.

According to the invention, "ammonium" denotes any desired substituted or unsubstituted ammonium group, in particular —$NH_3^{(+)}$, —$NH_2(C_{1-18}$-alkyl$)^{(+)}$, —$NH(C_{1-18}$-alkyl$)_2^{(+)}$ or —$N(C_{1-18}$-alkyl$)_3^{(+)}$, According to the invention, "sulfato" in particular denotes —O—S(O)$_2$—O—R, "sulfo" denotes —S(O)$_2$—O—R, "amidosulfo" denotes —O—S(O)$_2$—NR$_2$, "phosphato" denotes —O—P(O)(OR)$_2$, "phosphono" denotes —P(O)(OR)$_2$, "amidophosphono" denotes —O—P(O)(NR$_2$)$_2$ or —O—P(O)(OR)(NR$_2$) and "amidocarbonyl" denotes —C(O)—NR$_2$, R in each case mutually independently denote H, $M^{(+)}$, $C_{1-18}$ alkyl, $C_{6-10}$ aryl or $C_{1-18}$-alkyl-$C_{6-10}$-aryl.

The metal-ligand complex according to the invention preferably comprises a complex with a metal selected from Ag, Al, Ce, Co, Cu, Fe, Mo, Mn, Ni, Pb, Re, Ti, V and Zn in any desired oxidation state, the metal preferably being selected from Co(II), Co(III), Cu(I), Cu(II), Fe(II), Fe(III), Mn(II), Mn(III), Ni(II), Pb(II) and Zn(II), particularly preferably from Mn(II) and Mn(III).

The metal-ligand complex may generally be produced simply by mixing a metal salt of the corresponding metal with the corresponding ligand in an aqueous medium. Emergence of a desired oxidation state may be favored by establishing a suitable redox potential.

Any desired counterion, in particular acetate, tetrafluoroborate, fluoride, bromide, iodide or chloride, may in principle be considered for saturating any free valencies and/or free charges still remaining after attachment to the ligands.

The present invention likewise further provides the use of washing or cleaning agents according to the invention for cleaning textile fabrics and for cleaning hard surfaces.

The present invention likewise provides the above-stated ligands and metal-ligand complexes according to the invention as such. The metal-ligand complexes according to the invention are hereinafter also referred to as "bleach catalysts according to the invention".

The present invention in particular provides metal-ligand complexes of biheteroaryl ligands of the general formula (IV), preferably of biheteroaryl ligands of the general formula (V),
wherein the transition metal is selected from Ag, Al, Ce, Co, Cu, Fe, Mo, Mn, Pb, Re, Ti, V and Zn in any desired oxidation state, in particular from Co(II), Co(III), Cu(I), Cu(II), Fe(II), Fe(III), Mn(II), Mn(III), Pb(II) and Zn(II), particularly preferably from Mn(II) and Mn(III),
and wherein at least one substituent comprises an ammonium, hydroxycarbonyl, alkoxycarbonyl, aryloxycarbonyl, amidocarbonyl, halogen, nitro, sulfato, sulfo, amidosulfo, phosphate, phosphono, amidophosphono, hydroxy, alkoxy, amino or polyoxyethylene residue, in particular —(CH$_2$—CH$_2$—O—)$_n$— with n=1 to 20, preferably 3 to 20, is attached to the ligand skeleton, the substituents in a preferred embodiment in particular possibly comprising the particular residue itself or an alkyl group onto which the particular residue is attached, such that the substituent is preferably selected from sulfo, sulfoalkyl, in particular sulfo-$C_{1-18}$-alkyl, hydroxycarbonyl, hydroxycarbonylalkyl, in particular hydroxycarbonyl-$C_{1-18}$-alkyl, phosphono, phosphonoalkyl, in particular phosphono-$C_{1-18}$-alkyl, hydroxy, hydroxyalkyl, in particular hydroxy-$C_{1-18}$-alkyl, amino, aminoalkyl, in particular amino-$C_{1-18}$-alkyl, halogen, haloalkyl, in particular halo-$C_{1-18}$-alkyl, —(CH$_2$—CH$_2$—O—)$_n$H and $C_{1-18}$-alkyl-(CH$_2$—CH$_2$—O—)$_n$H with n in each case being 1 to 20, preferably 3 to 20.

The present invention furthermore also provides the use of ligands and/or metal-ligand complexes according to the invention in washing or cleaning agents, in particular for cleaning textile fabrics and for cleaning hard surfaces.

The present invention furthermore also provides the use of ligands and/or metal-ligand complexes according to the invention, in particular as auxiliaries, for cleaning textile fabrics and for cleaning hard surfaces.

The present invention furthermore also provides the use of ligands and/or metal-ligand complexes according to the invention for bleaching woodpulp and/or raw cotton.

The washing or cleaning agents according to the invention may comprise any conceivable type of cleaning agent, both as concentrates and as agents for undiluted use, for use on a commercial scale, in washing machines or in manual washing or cleaning. They include for example detergents for textiles, carpets or natural fibers and, that, according to the present invention, are designated as washing agents. They also include for example dishwashing agents for dishwashing machines or manual dishwashing agents or cleaning agents for hard surfaces such as metal, glass, porcelain, ceramics, glazed tiles, stone, coated surfaces, plastics, wood or leather; these are designated cleaning agents according to the present invention. More broadly, sterilizing agents and disinfectants should also be considered to be washing or cleaning agents for the purposes of the invention.

Embodiments of present invention comprise any presentations of the washing or cleaning agents according to the invention which are established in the prior art and/or are convenient. These include for example solid, pulverulent, liquid, gel-form or pasty preparations, optionally also comprising two or more phases, compressed or uncompressed; they furthermore include extrudates, granules, tablets or pouches, packaged both in large containers and in portions.

In a preferred embodiment, the washing or cleaning agents according to the invention contain the above-described bleach catalysts according to the invention in a quantity of up to 5 wt. %, in particular of 0.001 wt. % to 1 wt. % and particularly preferably of 0.01 wt. % to 0.5 wt. %, above all of 0.01 to 0.25 wt. %, in each case relative to the total weight of the washing or cleaning agents.

Apart from the bleach catalysts according to the invention, the agents according to the invention may optionally additionally also contain other bleach catalysts. These substances may generally comprise any desired bleach-boosting transition metal salt or any desired transition metal complex. Transition metals which may in particular be considered for this purpose are Mn, Fe, Co, Ru, Mo, Ti, V or Cu in various oxidation states. Possible complexing ligands which may in particular be considered, are, as described in the literature, guanidines, aminophenols, amine oxides, salenes, saldimines, lactams, monocyclic and cross-bridged polycyclic polyazaalkanes, terpyridines, dendrimers, tetraamido ligands, bis- and tetrakis(pyridylmethyl)alkylamines, secondary amines and polyoxometallates.

In a preferred embodiment, a complex of manganese in oxidation state II, III, IV or V, which preferably contains one or more macrocyclic ligands with the donor functions N, NR, PR, O and/or S, is used as an additional bleach catalyst. Ligands which comprise nitrogen donor functions are preferably used for this purpose. It is here particularly preferred additionally to use a bleach catalyst in the agents according to the invention which, as macromolecular ligands, contain 1,4,7-trimethyl-1,4,7-triazacyclononane (Me-TACN), 1,4,7-triazacyclononane (TACN), 1,5,9-trimethyl-1,5,9-triazacyclododecane (Me-TACD), 2-methyl-1,4,7-trimethyl-1,4,7-triazacyclononane (Me/Me-TACN) and/or 2-methyl-1,4,7-triazacyclononane (Me/TACN). Suitable manganese complexes are for example $[Mn^{III}_2(\mu\text{-O})_1(\mu\text{-OAc})_2(TACN)_2](ClO_4)_2$, $[Mn^{III}Mn^{IV}(\mu\text{-O})_2(\mu\text{-OAc})_1(TACN)_2](BPh_4)_2$, $[Mn^{IV}_4(\mu\text{-O})_6(TACN)_4](ClO_4)_4$, $[Mn^{III}_2(\mu\text{-O})_1(\mu\text{-OAc})_2(Me\text{-TACN})_2](ClO_4)_2$, $[Mn^{III}Mn^{IV}(\mu\text{-O})_1(\mu\text{-OAc})_2(Me\text{-TACN})_2](ClO_4)_3$, $[Mn^{IV}_2(\mu\text{-O})_3(Me\text{-TACN})_2](PF_6)_2$ and $[Mn^{IV}_2(\mu\text{-O})_3(Me/Me\text{-TACN})_2](PF_6)_2$ $(OAc=OC(O)CH_3)$.

When used, the additional bleach catalyst is also preferably present in the agents according to the invention in a quantity of up to 5 wt. %, in particular of 0.0025 wt. % to 1 wt. % and particularly preferably of 0.01 wt. % to 0.25 wt. %, in each case relative to the total weight of the washing or cleaning agent.

The washing or cleaning agent according to the invention furthermore preferably contains bleaching agents which preferably are and/or release the substrate for the bleach catalysts according to the invention. A bleaching agent should for this purpose be understood to mean, on the one hand, hydrogen peroxide itself and, on the other hand, any compound which releases hydrogen peroxide in an aqueous medium. Among those compounds acting as bleaching agents which release $H_2O_2$ in water, sodium percarbonate, sodium perborate tetrahydrate and sodium perborate monohydrate are of particular significance. Further usable bleaching agents are for example peroxypyrophosphates, citrate perhydrates and $H_2O_2$-releasing peracid salts or peracids, such as persulfates or persulfuric acid. The urea peroxyhydrate percarbamide, which can be described by the formula $H_2N\text{—}CO\text{—}NH_2.H_2O_2$, is also usable. In particular when using the agents for cleaning hard surfaces, for example in automatic dishwashing, they may if desired also contain bleaching agents from the group of organic bleaching agent, although the use thereof is in principle also possible in textile washing agents. Typical organic bleaching agents are diacyl peroxides, such as for example dibenzoyl peroxide. Further typical organic bleaching agents are peroxy acids, with examples which may in particular be mentioned being alkylperoxy acids and arylperoxy acids. Preferred representatives are (a) not only peroxybenzoic acid and the ring-substituted derivatives thereof, such as alkylperoxybenzoic acid, but also peroxy-α-naphthoic acid and magnesium monoperphthalate, (b) aliphatic or substitutedly aliphatic peroxy acids, such as peroxylauric acid, peroxystearic acid, ε-phthalimidoperoxycaproic acid (phthaloimino-peroxyhexanoic acid, PAP), o-carboxybenzamidoperoxycaproic acid, N-nonenyl-amidoperadipic acid and N-nonenylamidopersuccinates, and (c) aliphatic and aralphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-diacid, N,N-terephthaloyl-di(6-aminopercaproic acid).

Substances which release chlorine or bromine may also be used as bleaching agents. Examples of suitable materials which release chlorine or bromine and may be considered are heterocyclic N-bromamides and N-chloramides, for example trichloroisocyanuric acid, tribromoisocyanuric acid, dibromoisocyanuric acid and/or dichloroisocyanuric acid (DICA) and/or the salts thereof with cations such as potassium and sodium. Hydantoin compounds, such as 1,3-dichloro-5,5-dimethylhydanthoin are likewise suitable.

In one particular embodiment according to the invention, hydrogen peroxide-releasing substances are not used and oxygen is instead used as the bleaching agent, the oxygen possibly comprising atmospheric oxygen or oxygen which is liberated from an oxygen-releasing agent.

Washing or cleaning agents, in particular automatic dishwashing agents which are preferred according to the invention are those which contain up to 45 wt. %, in particular 1 to 35 wt. %, preferably 2.5 to 30 wt. %, particularly preferably 3.5 to 20 wt. % and in particular 5 to 15 wt. % of bleaching agent, preferably sodium percarbonate.

The active oxygen content of the washing or cleaning agent, in particular automatic dishwashing agent, amounts, in each case relative to the total weight of the agent, preferably to between 0.4 and 10 wt. %, particularly preferably to between 0.5 and 8 wt. % and in particular to between 0.6 and 5 wt. %. Particularly preferred agents have an active oxygen content of above 0.3 wt. %, preferably of above 0.7 wt. %, particularly preferably of above 0.8 wt. % and in particular of above 1.0 wt. %.

Alternatively to or also simultaneously with the bleaching agents, enzymes which are capable of producing hydrogen peroxide in situ from other substrates may also be used to supply the hydrogen peroxide. These comprise oxidoreductases which are capable of transferring electrons from, in general, an organic substrate, for instance glucose, to oxygen as electron acceptor and so permitting in situ formation of the desired hydrogen peroxide. The oxidoreductase may here be used together with the appropriate organic substrate. Since the soiling to be treated may, however, already contain the necessary substrate, the oxidoreductases may optionally also be used without addition of the appropriate substrate.

The hydrogen peroxide-producing oxidoreductase preferably comprises an oxidoreductase which produces hydrogen peroxide by using oxygen as the electron acceptor. Enzymes which may in particular be considered are oxidoreductases of EC classes EC 1.1.3 (CH—OH as electron donor), EC 1.2.3 (aldehyde or oxo group as electron donor), EC 1.4.3 (CH—$NH_2$ as donor), EC 1.7.3 (nitrogenous group as donor) and EC 1.8.3 (S-containing group as donor), enzymes of EC class EC 1.1.3 being preferred.

Preferred enzymes are in particular selected from the group consisting of malate oxidase (EC 1.1.3.3), glucose oxidase (EC 1.1.3.4), hexose oxidase (EC 1.1.3.5), cholesterol oxidase (EC 1.1.3.6), galactose oxidase (EC 1.1.3.9), pyranose oxidase (EC 1.1.3.10), alcohol oxidase (EC 1.1.3.13), choline oxidase (EC 1.1.3.17, see in particular WO 04/58955), oxidases for long-chain alcohols (EC 1.1.3.20), glycerol-3-phosphate oxidase (EC 1.1.3.21), cellobiose oxidase (EC 1.1.3.25), nucleoside oxidase (EC 1.1.3.39), D-mannitol oxidase (EC 1.1.3.40), xylitol oxidase (EC 1.1.3.41), aldehyde oxidase (EC 1.2.3.1), pyruvate oxidase (EC 1.2.3.3), oxalate oxidase (EC 1.2.3.4), glyoxylate oxidase (EC 1.2.3.5), indole-3-acetaldehyde oxidase (EC 1.2.3.7), pyridoxal oxidase (EC 1.2.3.8), aryl aldehyde oxidase (EC 1.2.3.9), retinal oxidase (EC 1.2.3.11), L-amino acid oxidase (EC 1.4.3.2), amine oxidase (EC 1.4.3.4, EC 1.4.3.6), L-glutamate oxidase (EC 1.4.3.11), L-lysine oxidase (EC 1.4.3.14), L-aspartate oxidase (EC 1.4.3.16), tryptophan alpha,beta-oxidase (EC 1.4.3.17), glycine oxidase EC 1.4.3.19), urea oxidase (EC 1.7.3.3), thiol oxidase (EC 1.8.3.2), glutathione oxidase (EC 1.8.3.3), sorbitol oxidase and from enzymes such as for instance described in DE102005053529.

In a preferred embodiment, the hydrogen peroxide-producing oxidoreductase is one which uses a sugar as electron donor. According to the invention, the hydrogen peroxide-producing and sugar-oxidizing oxidoreductase is preferably selected from glucose oxidase (EC 1.1.3.4), hexose oxidase (EC 1.1.3.5), galactose oxidase (EC 1.1.3.9) and pyranose oxidase (EC 1.1.3.10). Glucose oxidase (EC 1.1.3.4) is particularly preferred according to the invention.

When using a hydrogen peroxide-producing oxidoreductase, compounds, preferably organic compounds, particularly preferably aromatic compounds which interact with the enzymes, are advantageously also added in order to enhance the activity of the oxidoreductases in question (enhancers) or, in the event of a major difference in redox potential between the oxidizing enzymes and the soiling, to ensure electron flow (mediators).

The hydrogen peroxide-producing oxidoreductase, when used in the washing or cleaning agents according to the invention, is preferably used in a quantity such that the entire agent exhibits an oxidoreductase-related enzyme activity of 30 U/g to 20,000 U/g, in particular of 60 U/g to 15,000 U/g. The unit 1 U here corresponds to the activity of that quantity of enzyme which converts 1 μmol of its substrate at pH 7 and 25° C. in one minute.

The substrate which is optionally to be used when using such a hydrogen peroxide-producing oxidoreductase is generally directly indicated by the name of the particular oxidoreductase.

Agents according to the invention may optionally also contain bleaching activators as an additional bleaching auxiliary. Reference is made to published patent application WO2008/125590 with regard to bleaching activators which may preferably be used according to the invention and the preferred quantities thereof to be used.

Apart from a bleach catalyst according to the invention and the above-stated bleaching agent and any optionally present further bleaching auxiliaries, a washing or cleaning agent according to the invention optionally contains further ingredients such as further enzymes, enzyme stabilizers, surfactants, in particular nonionic, anionic, cationic and/or amphoteric surfactants, builder substances (builders, cobuilders), polymers, solvents, thickeners, sequestering agents, electrolytes, acidifying agents, optical brighteners, graying inhibitors, glass corrosion inhibitors, corrosion inhibitors, dye transfer inhibitors, foam inhibitors, disintegration auxiliaries, abrasives, dyes, fragrances, microbial active ingredients, UV absorbers, anticrease agents, antistatic agents, "soil release" active ingredients or soil repellents, propellants and optionally further conventional ingredients.

Reference is made to published patent application WO2008/125590 with regard to further enzymes, enzyme stabilizers, surfactants, builders, polymers, solvents, thickeners, sequestering agents, electrolytes, acidifying agents, optical brighteners, graying inhibitors, glass corrosion inhibitors, corrosion inhibitors, dye transfer inhibitors, foam inhibitors, disintegration auxiliaries, abrasives, dyes, fragrances, microbial active ingredients, UV absorbers, anticrease agents, antistatic agents, soil release active ingredients and propellants and the preferred quantities thereof to be used which may preferably be used according to the invention.

Particularly advantageous bleach catalyst granules have proved to be those which contain, relative to the total weight of the granules,
   a) 0.1 to 30 wt. % of a bleach catalyst according to the invention and optionally a further bleach catalyst,
   b) 10 to 99 wt. % of a support material, and
   c) 0.1 to 5 wt. % of a binder from the group of organic polymers.

The optionally used further bleach catalyst according to a) is here preferably selected from the further bleach catalysts which have already been stated above.

Suitable support materials b) are in principle any substances or mixtures of substances usable in washing or cleaning agents and compatible with the other ingredients, in particular the previously listed builders, especially carbonates, including hydrogencarbonates, sulfates, chlorides, silicates and phosphates. Suitable support materials are here in particular alkali metal carbonates, alkali metal hydrogencarbonates, alkali metal sesquicarbonates, alkali metal silicates, alkali metal metasilicates, alkali metal phosphates and mixtures of these substances, with alkali metal carbonates, in particular sodium carbonate, sodium hydrogencarbonate or sodium sesquicarbonate, and/or alkali metal phosphates preferably being used for the purposes of the present invention. In one particularly preferred embodiment, pentasodium triphosphate, $Na_5P_3O_{10}$ (sodium tripolyphosphate) or the corresponding potassium salt pentapotassium triphosphate, $K_5P_3O_{10}$ (potassium tripolyphosphate) is used as the support material.

The proportion by weight of the support material b) in the total weight of the bleach catalyst granules may be varied within the previously stated limits, with proportions by weight of above 20 wt. %, preferably of above 40 wt. % and in particular of above 60 wt. % having proved advantageous with regard to processability and actual bleaching performance after formulation with further ingredients with a washing and cleaning action. Consequently, bleach catalyst granules which are preferred for the purposes of the present application are those in which the proportion by weight of support material b) in the total weight of the granules amounts to 20 to 99 wt. %, preferably between 40 and 95 wt. % and in particular between 60 and 90 wt. %.

The bleach activator granules according to the invention contain a binder c) from the group of organic polymers as a third ingredient. The polymers may be of a nonionic, anionic, cationic or amphoteric nature. Natural polymers and modified polymers of natural origin may equally well be used as synthetic polymers.

Nonionic polymers belonging to the group of those which are particularly preferentially used as binder c) include polyvinyl alcohols, acetalized polyvinyl alcohols, polyvinylpyrrolidone and polyalkylene glycols, in particular polyethylene oxides. Preferred polyvinyl alcohols and acetalized polyvinyl alcohols exhibit molecular weights in the range from 10,000 to 100,000 gmol$^{-1}$, preferably of 11,000 to 90,000 gmol$^{-1}$, particularly preferably of 12,000 to 80,000 gmol$^{-1}$ and in particular of 13,000 to 70,000 gmol$^{-1}$. Preferred polyethylene oxides have molar masses in the range from approx. 200 to 5,000,000 g/mol, corresponding to degrees of polymerization n of approx. 5 to >100,000.

Anionic polymers belonging to the group of those which are particularly preferentially used as binder c) include in particular homo- or copolymeric polycarboxylates, polyacrylic acids and polymethacrylic acids, in particular those which have already previously been mentioned as organic builder materials usable for washing or cleaning agents, together with polymers containing sulfonic acid groups, in particular those which have already previously been mentioned as usable water-softening agents.

Reference is made to the polymers which have already previously been mentioned as polymers with a washing and cleaning action with regard to the group of cationic and amphoteric polymers which are particularly preferentially used as binder c).

In bleach catalyst granules which are preferred according to the invention, the proportion by weight of the binder c) in the total weight of the granules amounts to between 0.2 and 4.5 wt. %, preferably between 0.5 and 4.0 wt. % and in particular between 1.0 and 4.0 wt. %.

The bleach catalyst granules preferably have an average particle size of between 0.1 and 1.0 mm, particularly preferably of between 0.2 and 0.8 mm and in particular of between 0.3 and 0.7 mm, the proportion by weight of the particles with a particle size of below 0.1 mm preferably amounting to at least 4 wt. %, particularly preferably to at least 6 wt. % and in particular to at least 8 wt. %, while at the same time preferably amounting to at most 80 wt. %, particularly preferably to at most 60 wt. % and in particular to at most 40 wt. %, and the proportion by weight of particles with a particle size of between 0.2 and 0.8 mm preferably amounting to between 30 and 70 wt. %, particularly preferably to between 45 and 65 wt. % and in particular to between 40 and 60 wt. %.

Apart from the bleach catalyst, it is also possible to formulate enzymes or other, in particular sensitive, ingredients in the described manner.

The invention also independently provides methods for cleaning textiles or hard surfaces in which a bleach catalyst according to the invention is used in at least one of the method steps.

These include both manual and machine methods. Embodiments include for example manual washing, manual removal of stains/spots from textiles or hard surfaces or use in connection with a machine method, with machine methods being preferred, in particular for cleaning textiles, due to their being more precisely controllable, for example in terms of the quantities used and periods of action. The above-mentioned concentration ranges preferably apply correspondingly to these uses.

Cleaning of textile fabrics preferably proceeds at temperatures of 20-95° C., in a preferred embodiment at temperatures of 20-60° C., in particular at temperatures of 20-40° C., and preferably at a pH value of 5-12, in particular of 8-11.

Methods for cleaning textiles are in general distinguished in that in two or more method steps various substances with a cleaning action are applied onto the material to be cleaned and, after the exposure time, are washed off, or that the material to be cleaned is treated in some other manner with a washing agent or a solution of this agent. The same applies to methods for cleaning all materials other than textiles, which are grouped together below by the phrase "hard surfaces". Any conceivable washing or cleaning method may be enhanced in at least one of the method steps with a bleach catalyst according to the invention and then constitutes an embodiment of the present invention.

In a preferred embodiment of this use, the bleach catalysts according to the invention are here provided in the context of one of the above-stated formulations for agents according to the invention, preferably washing or cleaning agents.

The present invention also provides a product containing a composition according to the invention or a washing or cleaning agent according to the invention, in particular a cleaning product for hard surfaces according to the invention, and a spray dispenser. The product may here comprise both a single chamber and a multichamber container, in particular a two-chamber container. The spray dispenser is here preferably a manually actuated spray dispenser, in particular selected from the group comprising aerosol spray dispensers (pressurized gas container; also inter alia known as a spray can), self-pressurizing spray dispensers, pump spray dispensers and trigger spray dispensers, in particular pump spray dispensers and trigger spray dispensers with a container made from transparent polyethylene or polyethylene terephthalate. Spray dispensers are described in greater detail in WO 96/04940 (Procter & Gamble) and the US patents cited therein in relation to spray dispensers, to which full reference is made in this respect and the content of which is hereby incorporated into the present application. Trigger spray dispensers and pump atomizers have the advantage over pressurized gas containers that no propellant need be used. Suitable attachments, nozzles etc. ("nozzle-valves") on the spray dispenser through which particles can pass mean that an optionally present enzyme may in this embodiment optionally also be added to the agent in a form immobilized on particles and accordingly be dispensed as a cleaning foam.

Automatic dishwashing agents which are particularly preferred according to the invention comprise 5 to 70 wt. %, preferably 10 to 60 wt. % and in particular 20 to 50 wt. % of builder(s), with the exception of polymers with a washing and cleaning action;

2 to 28 wt. %, preferably 4 to 20 wt. % and in particular 6 to 15 wt. % of polymers with a washing and cleaning action;

0.5 to 10 wt. %, preferably 1 to 8 wt. % and in particular 2 to 6 wt. % of surfactant(s), preferably nonionic and/or amphoteric surfactant(s);

0.5 to 8 wt. %, preferably 1 to 7 wt. % and in particular 2 to 6 wt. % of enzyme(s);

2 to 20 wt. %, preferably 4 to 15 wt. % and in particular 6 to 12 wt. % of bleaching agent;

0.01 to 5 wt. %, preferably 0.02 to 4 wt. % and in particular 0.05 to 3 wt. % of bleach catalysts according to the invention; and optionally 0.01 to 5 wt. %, preferably 0.02 to 4 wt. % and in particular 0.05 to 3 wt. % of further bleach catalysts.

Very particularly preferred automatic dishwashing agents comprise 5 to 70 wt. %, preferably 10 to 60 wt. % and in particular 20 to 50 wt. % of phosphates;

2 to 28 wt. %, preferably 4 to 20 wt. % and in particular 6 to 15 wt. % of polymers with a washing and cleaning action;

0.5 to 10 wt. %, preferably 1 to 8 wt. % and in particular 2 to 6 wt. % of nonionic surfactant(s);

0.5 to 8 wt. %, preferably 1 to 7 wt. % and in particular 2 to 6 wt. % of enzyme(s) selected from amylases, proteases and amadoriases;

2 to 20 wt. %, preferably 4 to 15 wt. % and in particular 6 to 12 wt. % of percarbonate;

0.01 to 5 wt. %, preferably 0.02 to 4 wt. % and in particular 0.05 to 3 wt. % of bleach catalysts according to the invention; and optionally 0.01 to 5 wt. %, preferably 0.02 to 4 wt. % and in particular 0.05 to 3 wt. % of further bleach catalysts.

Automatic dishwashing agents according to the invention may be formulated in various ways. The agents according to the invention may assume the form of solid or liquid presentations and as a combination of solid and liquid presentations.

Suitable solid presentations are in particular powders, granules, extrudates or compacted products, in particular tablets. The liquid presentations based on water and/or organic solvents may be thickened, assuming gel form.

Agents according to the invention may be formulated in the form of monophasic or multiphasic products. Preferred automatic dishwashing agents are in particular those with one, two, three or four phases. Automatic dishwashing agents wherein they assume the form of a prefabricated dispensing unit with two or more phases are particularly preferred.

The individual phases of multiphasic agents may be of identical or different states of aggregation. Preferred automatic dishwashing agents are in particular those which comprise at least two different solid phases and/or at least two liquid phases and/or at least one solid and at least one liquid phase.

Automatic dishwashing agents according to the invention are preferably preformulated as dispensing units. These dispensing units preferably comprise the quantity of substances with a washing or cleaning action required for a washing operation. Preferred dispensing units have a weight of between 12 and 30 g, preferably of between 14 and 26 g and in particular of between 16 and 22 g.

The volume of the above-stated dispensing units and their three-dimensional shape are particularly preferentially selected such that the preformulated units can be dispensed by means of the dispensing chamber of a dishwashing machine. The volume of the dispensing unit therefore preferably amounts to between 10 and 35 mL, preferably between 12 and 30 mL and in particular between 15 and 25 mL.

The automatic dishwashing agents according to the invention, in particular the prefabricated dispensing units, particularly preferentially comprise a water-soluble covering.

The following examples illustrate the invention in greater detail without limiting it thereto.

EXEMPLARY EMBODIMENTS

Example 1

Preparation of 1,10-bis(2-hydroxyphenyl)phenanthroline H2(bpphen): 2,9-bis(2-methoxyphenyl)-1,10-phenanthroline[1]

$2C_7H_7BrO + 2 Li \rightarrow 2 C_7H_7OLi$
$2C_7H_7OLi + C_{12}H_6N_2 \rightarrow C_{26}H_{20}N_2O_2$ 60 g (0.32 mol) of bromoanisole are dissolved in 50 mL of ether and slowly added dropwise at 0° C. to a suspension of 8.9 g (1.28 mol) of lithium in 50 mL of ether. The reaction mixture is then raised to RT within one hour, after which it is refluxed for one hour. After cooling, excess lithium is separated with a reverse-sintered filter (Celite) and the solvent is removed from the filtrate under a vacuum. The remaining residue is redissolved in 100 mL of toluene and a solution of 4.56 g (23 mmol) of 1,10-phenanthroline * $H_2O$ in 150 mL of toluene is added dropwise at 0° C. to the resultant suspension of a virtually colorless solid in a yellowish solution. The resultant blood-red solution is raised to RT and refluxed for a further 5 h. After cooling, the mixture is quenched with 50 mL of water and extraction performed three times with 50 mL portions of dichloromethane. 120 g of $MnO_2$ are added, the resultant suspension is stirred for 4 h at RT, filtered through Celite and the solvent is removed from the filtrate. After column chromatography (silica gelt, eluent: ether/DCM, 20:1) the product is obtained as a pale yellow solid.

$^1$H-NMR (300 MHz, CDCl$_3$): δ=3.93 (s, 6H), 7.07 (d, 2H, $^3$J=8.31 Hz), 7.19 (t, 2H, $^3$J=7.56 Hz), 7.47 (t, 2H, $^3$J=7.75 Hz), 7.90 (s, 2H), 8.29 (dd, 2H, $^3$J=7.55 Hz, $^5$J=1.32 Hz), 8.44 (m, 4H) ppm.

Yield 2.36 g (26% of theoretical)

2,9-bis(2-hydroxyphenyl)-1,10-phenanthroline
$C_{26}H_{20}N_2O_2 \rightarrow C_{24}H_{16}N_2O_2$ 2.6 g (6 mmol) of 2,9-bis(2-methoxyphenyl)-1,10-phenanthroline are dissolved in 80 mL of DMF and 2.0 g of NaSEt (4 eq.) are added. The reaction mixture is refluxed for 4 h and, after cooling, combined with a mixture of 100 mL of 20% $H_2O_2$ solution and 100 mL of 10% NaOH solution, a bulky, yellow precipitate immediately forming.

After stirring for 20 min. at RT, the mixture is cautiously slightly acidified with dilute $H_2SO_4$(aq) (pH=~6) and extracted five times with 100 mL portions of DCM. The combined organic phases are washed with brine, dried over $Na_2SO_4$ and evaporated to approx. 100 mL. The product can be precipitated as a yellow solid by adding 400 mL of EtOH and cooling to −30° C. and separated by filtration.

Yield 1.27 g (58% of theoretical)

$^1$H-NMR (300 MHz, DMSO$_3$): δ=7.06 (m, 4H), 7.42 (t, 2H, $^3$J=7.27 Hz), 8.07 (s, 2H, 8.27 (d, 2H, $^3$J=7.93 Hz), 8.60 (d, 2H, $^3$J=8.68 Hz), 8.69 (d, 2H, $^3$J=8.68 Hz), 13.92 (s, 2H) ppm.

→Synthesis of the complex [Mn(bpphen)]Cl, see [1]

[1] S. Routier, V. Joanny, A. Zaparucha, H. Vezin, J.-P. Catteau, J.-L. Bernier, C. Bailly, J. Chem. Soc., Perkin Trans. 2, 1998, 863-868.

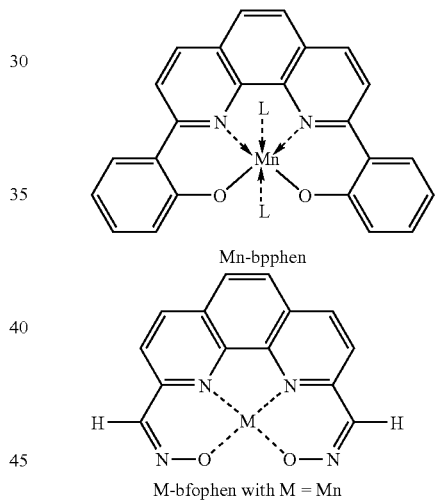

Mn-bpphen

M-bfophen with M = Mn

Example 2

Washing Test in Model Washing Installation

The washing test is performed in a temperature-controllable multistirrer. 1 l glass beakers containing an apparatus for mechanically stirring the washing liquor are used as the test vessels. The stirring mechanism is designed such that, on the one hand, all the beakers are stirred at the same speed and, on the other hand, the direction of stirring changes periodically. The washing chambers are filled with approx. 16 g of ballast laundry and approx. 6 g of soiled fabric (the fabric portions are cut into squares of an edge length of approx. 6 cm and consist of cotton). All the test fabrics are manufactured by CFT B.V. (Netherlands).

The soiled fabric comprise the following test substrates of relevance to bleaching:

| | |
|---|---|
| CS-103 | red wine |
| CS-3 | aged red wine |
| BC-1 | tea |
| BC-3 | tea |
| CS-15 | blueberry juice |

A set of eight soiled fabric portions is prepared from these 5 test fabrics for testing. This means that three of the types of soiling are represented twice in the test.

Bleaching performance is determined by measuring the tristimulus value Y (lightness value) of the bleached fabric and making a comparison with the reference sample. The tristimulus value Y is calculated from the measured L value by the following mathematical equation:

$$L = 116(Y/Y_n)^{1/3} - 16$$

L values are measured with a Minolta CM-508d spectrophotometer. Essentially two washing test scenarios are used for determining bleaching activity. On the one hands washing test with a complete washing agent formulation without TAED (washing with complete washing agent without TAED) and, on the other hand, a simplified washing test comprising only hydrogen peroxide and surfactants ($H_2O_2$ test). The following test parameters are used in the washing test with complete washing agent without TAED:

Volume of agent solution: 750 mL
Quantity of washing agent with TAED: (100 g of complete washing agent per 16 l of liquor, consequently 4.69 g per 750 mL)
Quantity of washing agent without TAED: 4.55 g per 750 mL
Metal catalyst: 0.0086 mmol per transition metal atom
Temperature: 30° C.
Washing time: 60 min
Rinsing volume: 500 mL
Rinsing time: 15 min
Water quality: artificially hardened deionized water with
  $CaCl_2 \times 2H_2O$ (8.73 g per 25 l) and
  $MgCl_2 \times 6H_2O$ (2.42 g per 25 l)=16 German hardness degrees) pH value 10.5 (carbonate buffer solution)

The following table shows the washing results for the various transition metal complexes in the complete washing agent without TAED. The value for the complete washing agent without TAED and without transition metal complexes ("without catalyst") and the value for the complete washing agent with TAED are stated as comparison values.

TABLE 1

| Washing test with complete washing agent without TAED | |
|---|---|
| Mn-bpphen | 75 |
| Mn-bfophen | 74 |
| without catalyst | 71.7 |
| TAED | 75.8 |

The following test parameters are used in the simplified washing test ($H_2O_2$ test):
Volume of agent solution: 750 mL
Quantity of $H_2O_2$: 10 mmol per l
Surfactants: LAS=0.58 g; LT07=0.12 g
Metal catalyst: 0.0086 mmol per transition metal atom
Temperature: 30° C.
Washing time: 60 min
Water quality: deionized water
pH value 10.5 (carbonate buffer solution)

The following table shows the washing results for the various transition metal complexes according to the simplified washing test ($H_2O_2$ test).

TABLE 2

| Simplified washing test ($H_2O_2$ test) | |
|---|---|
| Mn-bpphen | 75 |
| M-bfophen | 75 |

The invention claimed is:

1. An agent for washing or cleaning a textile fabric, the agent comprising at least one component selected from the group consisting of ligands of the general formula (I), ligand-metal complexes of ligands of the general formula (I), and combinations thereof:

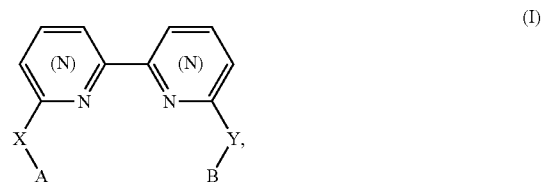

(I)

wherein X and Y each independently represent a moiety selected from the group consisting of ethyl, ethenyl, —CH=N—, —C($C_{1-18}$-alkyl)=N—, cycloalkyl, cycloheteroalkyl, $C_{6-10}$ aryl and heteroaryl, wherein A and B each independently represent a substituent selected from the group consisting of OH, SH, $NH_2$, NH($C_{1-18}$-alkyl) or —N($C_{1-18}$-alkyl)$_2$, in which A is linked by X and B by Y to the biheteroaryl residue via 2 atoms, and in which a so formed skeleton can also be bridged as well as mono- or polysubstituted; and
a surfactant.

2. The agent according to claim 1, wherein the at least one component is selected from the group consisting of ligands of the general formula (II), ligand-metal complexes of ligands of the general formula (II), and combinations thereof:

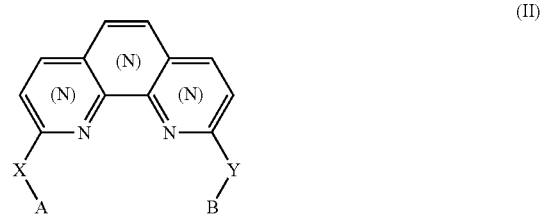

(II)

in which the so formed skeleton can also be mono- or polysubstituted.

3. The agent according to claim 1, wherein X and Y each independently represent a $C_{6-10}$ aryl or heteroaryl, and A and B each independently represent OH or SH.

4. The agent according to claim 1, wherein X and Y each independently represent a moiety selected from optionally substituted benzene, naphthalene, pyrrole, furan, thiophene, pyridine, pyrimidine, pyrazine, pyrone, pyridone, purine, triazine, imidazole, thiazole, oxazole, indole, quinoline, isoquinoline, benzimidazole, benzothiazole and benzoxazole.

5. The agent according to claim 1, wherein the at least one component is selected from the group consisting of ligands of the general formula (III), ligand-metal complexes of ligands of the general formula (III), and combinations thereof:

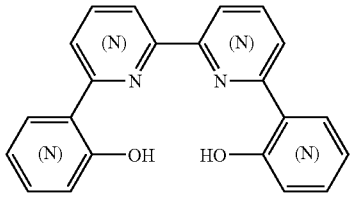
(III)

in which the so formed skeleton can also be bridged as well as mono- or polysubstituted.

6. The agent according to claim 5, wherein the ligands are ligands of the general formula (IV)

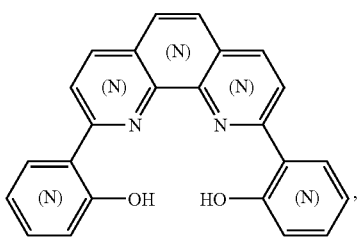
(IV)

in which the skeleton can also be mono- or polysubstituted.

7. The agent according to claim 6, wherein the ligands are ligands of the general formula (V)

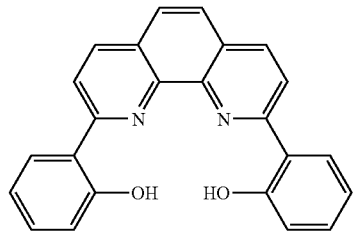
(V)

in which the skeleton can also be mono- or polysubstituted.

8. The agent according to claim 1, wherein the skeleton of the ligand bears as substituent at least one residue comprising a group selected from ammonium, hydroxycarbonyl, alkoxycarbonyl, aryloxycarbonyl, amidocarbonyl, halogen, nitro, sulfato, sulfo, amidosulfo, hydroxyl, phosphono, amidophosphono, hydroxyl, alkoxy, amino and polyoxyethylene.

9. The agent according to claim 1, wherein the at least one component comprises a metal-ligand complex of ligands of the general formula (I) comprising a metal selected from the group consisting of Ag, Al, Ce, Co, Cu, Fe, Mo, Mn, Ni, Pb, Re, Ti, V and Zn in any oxidation state.

10. A method comprising: (a) providing a textile fabric; and (b) contacting the textile fabric with an agent according to claim 1.

11. A method comprising: (a) providing a textile fabric; and (b) contacting the textile fabric with an agent according to claim 2.

12. A method comprising: (a) providing a textile fabric; and (b) contacting the textile fabric with an agent according to claim 5.

* * * * *